(12) United States Patent
Lim et al.

(10) Patent No.: US 9,604,049 B2
(45) Date of Patent: Mar. 28, 2017

(54) IMPLANTABLE MEDICAL LEADS HAVING OSCILLATING CABLE CONDUCTOR LUMENS

(71) Applicant: Cardiac Pacemakers, Inc., St. Paul, MN (US)

(72) Inventors: Lily Lim, Minneapolis, MN (US); Devon N. Arnholt, Shoreview, MN (US); Joel T. Eggert, Plymouth, MN (US); Andrew De Kock, Andover, MN (US); Paul E. Zarembo, Vadnais Heights, MN (US); Christopher A. Hartemink, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/942,766

(22) Filed: Nov. 16, 2015

(65) Prior Publication Data

US 2016/0067475 A1 Mar. 10, 2016

Related U.S. Application Data

(62) Division of application No. 14/508,087, filed on Oct. 7, 2014, now Pat. No. 9,216,281, which is a division of application No. 13/688,016, filed on Nov. 28, 2012, now Pat. No. 8,886,336.

(60) Provisional application No. 61/564,431, filed on Nov. 29, 2011.

(51) Int. Cl.
*A61N 1/05* (2006.01)
*B29C 45/14* (2006.01)

(52) U.S. Cl.
CPC .......... *A61N 1/05* (2013.01); *B29C 45/14065* (2013.01); *B29C 45/14262* (2013.01); *B29C 45/14819* (2013.01); *Y10T 29/49204* (2015.01)

(58) Field of Classification Search
CPC ............... A61N 1/15; B26C 45/14065; B26C 45/14262; B26C 45/14819; Y10T 29/49206
USPC ........................................................ 607/116
See application file for complete search history.

(56) References Cited

U.S. PATENT DOCUMENTS

| | | | |
|---|---|---|---|
| 5,324,321 A | 6/1994 | Pohndorf et al. |
| 6,249,708 B1 | 6/2001 | Nelson et al. |
| 7,184,838 B2 | 2/2007 | Cross, Jr. |
| 7,395,116 B2 | 7/2008 | Mehdizadeh et al. |
| 7,680,544 B1 | 3/2010 | Conger |
| 8,886,336 B2 | 11/2014 | Lim et al. |
| 9,216,281 B2 | 12/2015 | Lim et al. |
| 2007/0282410 A1 | 12/2007 | Cross, Jr. et al. |

(Continued)

*Primary Examiner* — Paula J Stice
(74) *Attorney, Agent, or Firm* — Faegre Baker Daniels LLP

(57) ABSTRACT

An electrical implantable lead includes an elongated lead body having a plurality of lumens therein, including at least one linear lumen and at least one planar, non-linear lumen and a plurality of conductor cables disposed within the plurality of lumens. The electrical implantable lead further includes a terminal connector coupled to a proximal end of the lead body, the terminal connector being in electrical communication with at least one of the plurality of conductor cables. Further, the electrical implantable lead includes at least one electrode coupled to the lead body, the at least one electrode in electrical communication with at least one of the plurality of conductor cables. In accordance with various embodiments, the at least one non-linear lumen extends longitudinally along a portion of the lead body and includes a plurality or crests and a plurality of troughs.

20 Claims, 13 Drawing Sheets

(56) References Cited

U.S. PATENT DOCUMENTS

2012/0136419 A1   5/2012   Zarembo et al.

IMPLANTABLE MEDICAL LEADS HAVING OSCILLATING CABLE CONDUCTOR LUMENS

CROSS-REFERENCE TO RELATED APPLICATION

This application is a division of U.S. application Ser. No. 14/508,087, filed Oct. 7, 2014, now U.S. Pat. No. 9,216,281, which is a division of U.S. application Ser. No. 13/688,016, filed Nov. 28, 2012, now U.S. Pat. No. 8,886,336, which claims the benefit of U.S. Provisional Application No. 61/564,431, filed Nov. 29, 2011, which are herein incorporated by reference in their entirety.

TECHNICAL FIELD

The present invention relates to medical devices. More specifically, the invention relates to an elongate implantable medical lead and methods of manufacturing the medical lead.

BACKGROUND

Implantable medical leads are devices that deliver electrical signals to implantable medical devices. Exemplary implantable devices are cardiac rhythm management (CRM) systems (e.g., pacemakers, defibrillators, and cardiac resynchronization therapy devices) and neurostimulation systems (e.g., spinal cord stimulation (SCS) systems). For CRM systems, medical leads are typically advanced intravascularly to an implant location within or on a patient's heart, while for neurostimulation systems, such leads are typically positioned beneath the skin, in vessels located in the neck or limbs, in the pectoral region, in the epidural space of the spinal cord, or intramuscularly.

Implantable leads typically include a flexible conductor surrounded by an insulating tube or shaft that extends from an electrode at the distal end to a connector terminal at the proximal end. Many leads incorporate multiple connectors extending from an electrical contact on a connector terminal to an electrode on a distal end of the lead body. When the connector terminal is coupled to an implantable device, and the device and lead are implanted in a patient, certain stresses or strains may develop in portions of the lead body or conductors near the terminal connector, or regions of a lead that experience bending.

SUMMARY

In Example 1, the present invention is an implantable medical lead including an elongated lead body having a plurality of lumens therein, including at least one linear lumen and a first non-linear lumen. A plurality of conductor cables are disposed within the plurality of lumens. The implantable medical lead further includes a terminal connector coupled to a proximal end of the lead body, the terminal connector in electrical communication with at least one of the plurality of conductor cables. Further, the implantable lead includes at least one electrode coupled to the lead body, the at least one electrode in electrical communication with at least one of the plurality of conductor cables. The first non-linear lumen extends longitudinally along a portion of the lead body and includes a plurality of crests and a plurality of troughs.

Example 2 is the implantable medical lead of Example 1, further comprising a second non-linear lumen extending longitudinally along a portion of the lead body.

Example 3 is the implantable medical lead of either Examples 1 or 2, wherein the plurality of lumens have a circular cross-section.

Example 4 is the implantable medical lead of any of the Examples 1-3, wherein the first and second non-linear lumens are offset from a central axis of the elongated lead body.

Example 5 is the implantable lead of any of the Examples 1-4, wherein the series of crests and troughs define a sinusoidal pattern with a defined amplitude and a defined frequency.

Example 6 is the implantable lead of any of the Examples 1-5, wherein the defined amplitude is between about 10 and about 50 mm and further wherein the defined angular frequency is between about 0.1 and about 0.7 mm.

Example 7 is the implantable lead of any of the Examples 1-6, wherein the series of crests and troughs are formed in a linear plane in a two-dimensional manner.

Example 8 is the implantable lead of any of the Examples 1-7, wherein the series of crests and troughs are formed in a rotational plane in a three-dimensional manner.

Example 9 is the implantable lead of any of the Examples 1-8, wherein the first non-linear lumen and the second non-linear lumen have equal frequencies and amplitudes.

Example 10 is the implantable lead of any of the Examples 1-9, wherein the first non-linear lumen has a first frequency and the second non-linear lumen has a second frequency that is not equal to the first frequency.

Example 11 is the implantable lead of any of the Examples 1-10, wherein the first non-linear lumen extends along the portion of the lead body extending about 10 to about 50 mm from the terminal connector.

In Example 12, the present invention is a method of manufacturing an implantable medical lead. The method includes extruding a polymeric material through a die configured to create a plurality of lumens within the implantable electrical lead. The plurality of lumens extend along a longitudinal axis of the die. The method also includes twisting the die with respect to the longitudinal axis alternatively in a clockwise and a counterclockwise direction while extruding such that twisting in the clockwise direction creates a trough and in the counterclockwise direction creates a crest in the plurality of lumens. The method further includes disposing a conductor cable in each of the plurality of the lumens.

In Example 13, the present invention is a method of manufacturing an implantable medical lead, which includes holding a cable in tension in a mold and adjusting the cable using a plurality of guiding pins to create a plurality of planar crests and troughs within the cable, and injecting a molten material into the mold to form a lead body around the cable, such that the cable extends longitudinally along a portion of the lead body.

Example 14 is the method of manufacturing an implantable medical lead of Example 13, further including removing the cable from the mold such that a lumen with the series of crests and troughs is created.

Example 15 is the method of manufacturing an implantable medical lead of Examples 13 or 14, wherein the cable is at least one of a conductor cable, a Nitinol wire, and a cable with a lubricious coating.

Example 16 is the method of manufacturing an implantable medical lead of any of Examples 13-15, further including filling holes created by the plurality of guiding pins with a molten material.

Example 17 is the method of manufacturing an implantable medical electrical lead of any of Examples 13-16, wherein the molten material is one of Liquid Silicone Rubber (LSR) and a medical adhesive.

Example 18 is the method of manufacturing an implantable medical lead of any of the Examples 13-17, wherein the molten material is LSR.

Example 19 is a method of manufacturing an implantable medical lead. The method includes providing a core pin made of a shape memory metal, the core pin having a first generally sinusoidal configuration and a second generally linear configuration, injecting silicone rubber having a durometer of between about Shore 60D and about Shore 40A over the core pin while in the first generally sinusoidal configuration to form a lead body, cooling the core pin such that the core pin is in the second generally linear configuration, removing the core pin from the lead body so that the lead body defines a lumen having a generally sinusoidal configuration, and inserting a conductor into the lumen.

Example 20 is an electrical implantable lead, wherein the implantable lead includes an elongated lead body having a plurality of lumens therein and a plurality of conductor cables disposed within the plurality of lumens. The plurality of conductor cables including at least one non-linear conductor cable. The electrical implantable lead further includes a terminal connector coupled to a proximal end of the lead body, the terminal connector being in electrical communication with at least one of the plurality of conductor cables. Further, the electrical implantable lead includes at least one electrode coupled to the lead body, the at least one electrode in electrical communication with at least one of the plurality of conductor cables. In accordance with various examples, the at least one non-linear conductor cable is configured to be disposed and extend longitudinally along a portion of the lead body and includes a plurality of crests and a plurality of troughs.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1A:
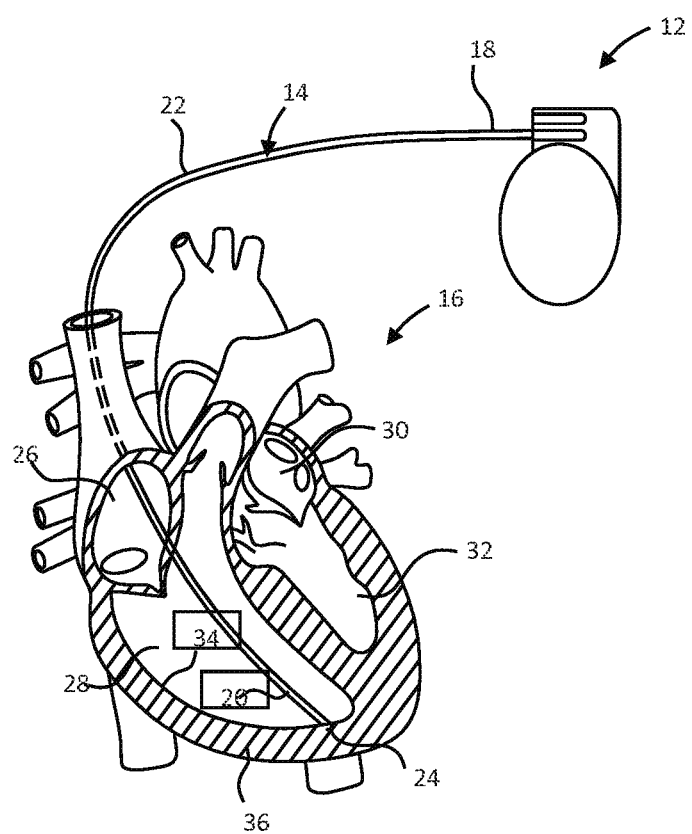
FIGS. 1A-1B are perspective views of an implantable medical device and an electrical implantable lead according to various embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1A is a perspective view of an implantable cardiac rhythm management (CRM) system 10. As shown, the system 10 includes an implantable rhythm management device 12 (e.g., a pulse generator) and an implantable electrical lead 14, which includes a lead body 22 that extends from a proximal portion 18 to a distal portion 20. As shown in FIG. 1, the heart 16 includes a right atrium 26, a right ventricle 28, a left atrium 30 and a left ventricle 32. As shown, the heart 16 includes an endocardium 34 covering the myocardium 36. In some embodiments, a fixation helix 24, located at an end of the distal portion 20 of the lead 14, penetrates through the endocardium 34 and is embedded in the myocardium 36. In some embodiments, the fixation helix 24 is electrically active and thus operates as a helical electrode for sensing the electrical activity of the heart 16 and/or applying a stimulating pulse to the right ventricle 28. In one embodiment, the CRM system 10 includes a plurality of leads 14. For example, it may include a first lead 14 adapted to convey electrical signals between the pulse generator 12 and the right ventricle 28 and a second lead (not shown) adapted to convey electrical signals between the pulse generator 12 and the right atrium 26 or coronary veins (not shown).

Figure 1B:
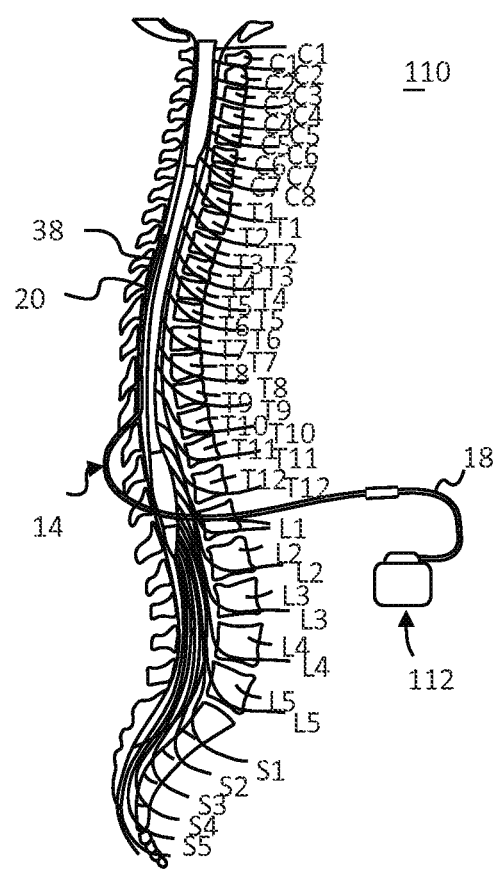

FIG. 1B is a perspective view of a representative implantable neurostimulation (e.g., spinal cord stimulation) system 110. As shown in FIG. 1B, C1-C8 are the cervical vertebrae and nerves, T1-T12 are the thoracic vertebrae and nerves, L1-L5 are the lumbar vertebrae and nerves, and S1-S5 are the sacrum and coccyx and the sacral nerves. Other implantable neurostimulation systems include deep brain stimulation and peripheral (e.g., vagal) nerve stimulation systems. As shown in FIG. 1B, a neurostimulation system 110 according to various embodiments includes an implantable device or pulse generator (IPG) 112 that generates electrical stimulation pulses used for stimulation. The IPG 112 is coupled to a lead 14 having a proximal portion 18 and a distal portion 20 extending to an electrode array 38 at or near an end of the distal portion 20. The electrical stimulation provided by the IPG 112 through the electrode array 38 may be used for numerous purposes including, for example, masking sensed pain.

Figure 2A:
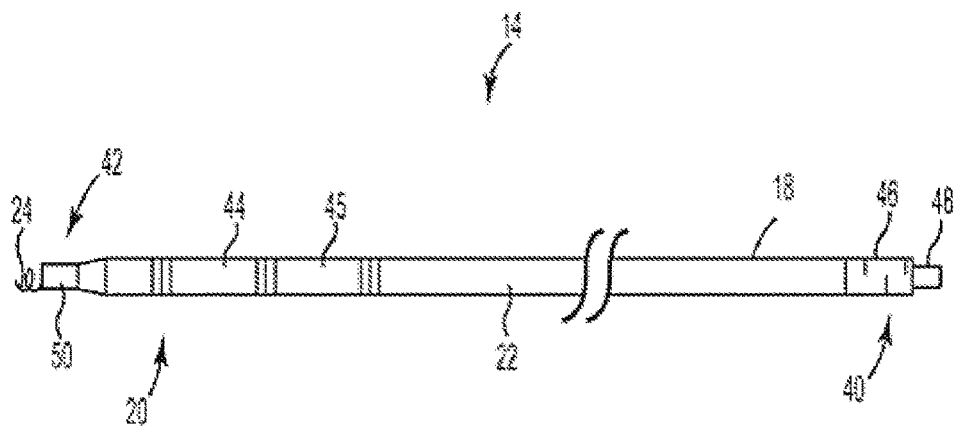
FIGS. 2A-2B are perspective views of the electrical implantable lead, according to various disclosed embodiments.

FIG. 2A is a perspective view of the lead 14, according to various disclosed embodiments, for use in an implantable system such as for example a CRM system 10 or a neurostimulation system 110. As shown, a connector assembly 40 is disposed at or near the proximal region 18 of the lead 14, while a distal assembly 42 is disposed at or near the distal portion 20 of the lead 14. Depending on the functional requirements of the system 10 (see FIG. 1A) or system 110 (see FIG. 1B) and the therapeutic needs of a patient, the distal portion 20 may include one or more electrodes. As shown, the distal portion 20 includes a pair of coil electrodes 44 and 45 that can function as shocking electrodes for providing a defibrillation shock to the heart or as low voltage pace or sense electrodes. Various electrode combinations may be incorporated into the lead 14 within the scope of the various embodiments of the present disclosure (e.g., one or more coil or ring electrodes). As shown in FIG. 2A, the connector assembly 40 includes a connector 46 and a terminal pin 48. The connector 46 is configured to be coupled to the lead body 22 and is configured to mechanically and electrically couple the lead 14 to a header on the pulse generator 12 (see FIG. 1A) or the IPG 112 (see FIG. 1B). As shown in FIG. 2A, the distal assembly 42 includes a radiopaque marker 50 and a fixation helix 24.

Figure 2B:
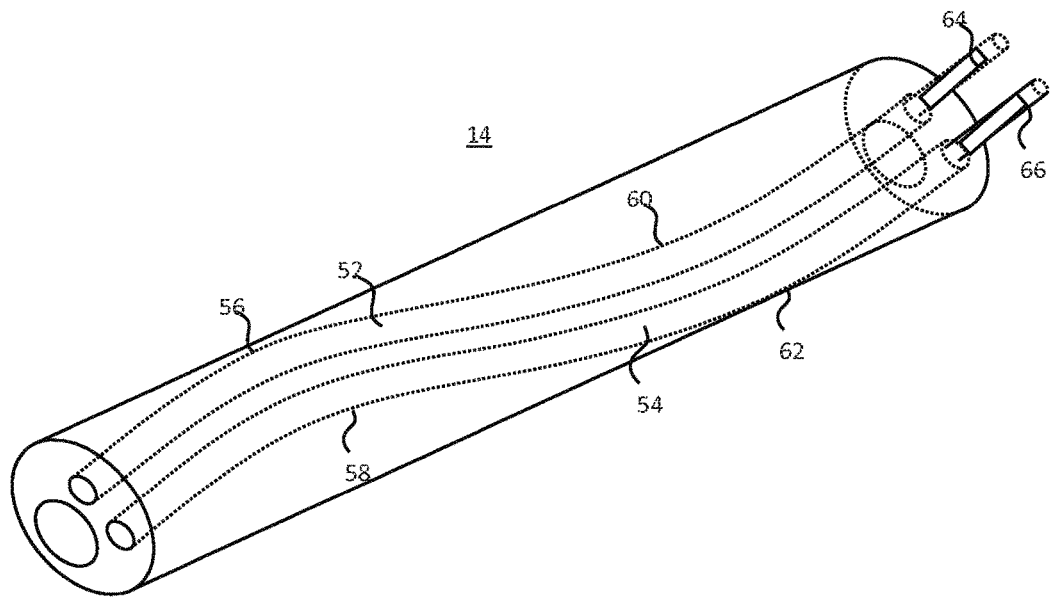

FIG. 2B illustrates a perspective view of a portion of the electrical implantable lead 14 according to various embodiments. The electrical implantable lead 14 may be interchangeably referred to as lead 14. The lead 14 includes an elongated lead body having one or more lumens 52 and 54 extending longitudinally along a portion or substantially the entire length of the lead 14 in a non-linear fashion. The non-linear path defined by the lumens 52 and 54 may have several configurations, including for example oscillating, waveform-shaped, or W-shaped. As shown in FIG. 2B, the lumens 52 and 54 have a series of crests and troughs including crests 56, 58 and troughs 60, 62. According to various embodiments, the lumens 52 and 54 extend in different planes longitudinally along the lead 14. In other embodiments of the invention, the crests and troughs extend longitudinally along the lead 14 in the same or substantially the same plane. Many embodiments disclosed herein refer to a lead 14 including lumens 52 and 54 having a non-linear or oscillating shape. Each such embodiment includes an alternative embodiment in which the lead 14 does not includes lumens, but instead the lead 14 is formed directly around a conductor (e.g., a cable conductor), such that no lumen is formed.

In various embodiments, one or both of the lumens 52 and 54 extend longitudinally along the lead 14 along a three-dimensional path, including for example a generally spiral or generally helical path. Also, in some embodiments, one or both of the crests and troughs of the lumens 52 and 54 may define a waveform shape having a variable amplitude and/or a variable frequency. In other embodiments, the lumens 52 and 54 may have a constant amplitude and frequency. Further, the lead 14 may include a plurality of conductor cables 64 and 66 disposed in the lumens 52 and 54 such that the lumen 52 includes a first conductor cable 64 and the lumen 54 includes a second conductor cable 66. According to some embodiments, each of the non-linear lumens have the same (or substantially the same) amplitude and angular frequency. According to other embodiments, the amplitude, the angular frequency, or both are different in one non-linear lumen as compared to another non-linear lumen.

The non-linear or oscillating path defined by the lumens 52 and 54 provides a slack to the conductor or cable by allowing for the length of the conductor or cable to exceed a corresponding length of the lead body. This slack in the conductor cables 64 and 66 may minimize strain and stress in the conductor cables 64 and 66 associated with flexural bending of the lead 14 in vivo. The portions of the lead body that may be optimized to provide increased amount of slack include, for example, the terminal flex region of a cardiac lead, the neck portion of vagal stimulation leads, material transition regions, or joints (e.g., polyurethane to silicone) along a lead body. Further, in embodiments of the present disclosure, the electrical implantable lead 14 are made of a polymeric material. It will be apparent to a person of ordinary skill in the art that the polymeric material for the electrical implantable lead 14 may be any known biocompatible polymeric material.

Figure 3A:
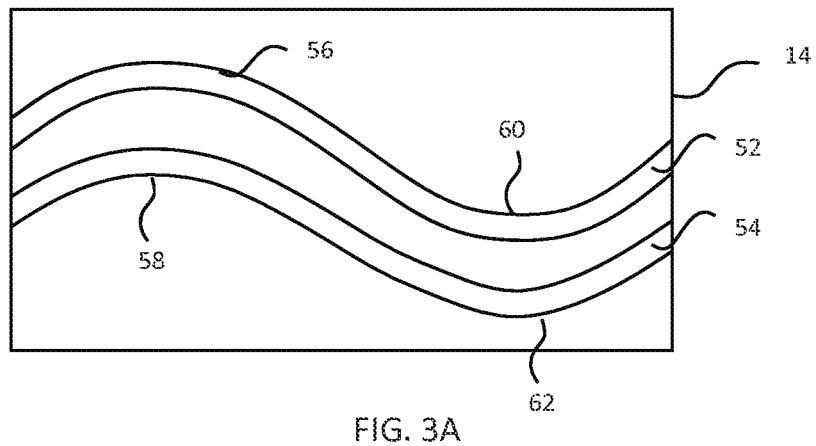
FIGS. 3A-3B illustrate schematic views of a portion of the electrical implantable lead with different orientations of the lumens according to various embodiments.
Figure 3B:
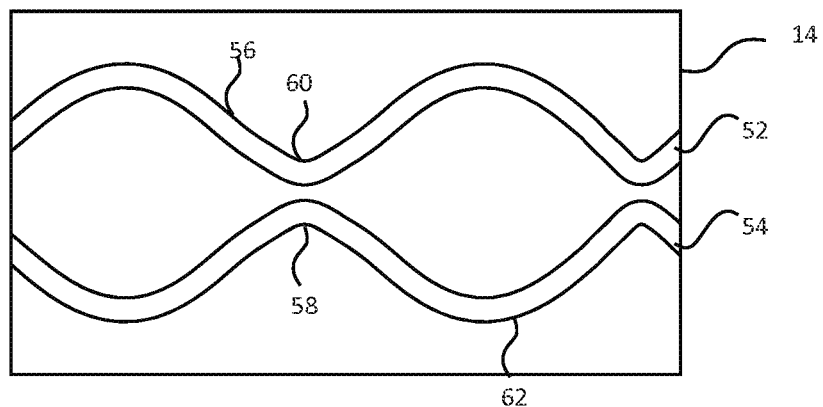

FIGS. 3A and 3B illustrate schematic views of a portion of the electrical implantable lead 14 with different orientations of the lumens 52 and 54 according to various embodiments. FIG. 3A illustrates a series of crests (including crests 56 and 58) and troughs (including troughs 60 and 62) in the lumens 52 and 54 that have equal (or substantially equal) amplitudes and magnitudes. FIG. 3B illustrates a series of crests (including crests 56 and 58) and troughs (including troughs 60 and 62) in the lumens 52 and 54 that have equal (or substantially equal) amplitudes but opposite magnitudes.

Figure 4A:
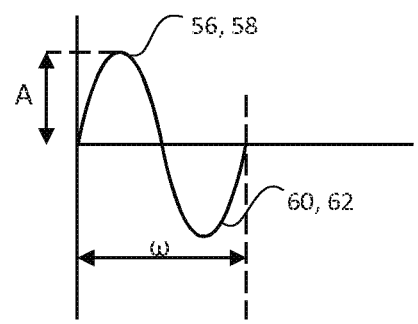
FIGS. 4A-4C illustrate different sinusoidal oscillations of different amplitudes and frequencies in lumens of the electrical implantable lead according to various embodiments.
Figure 4B:
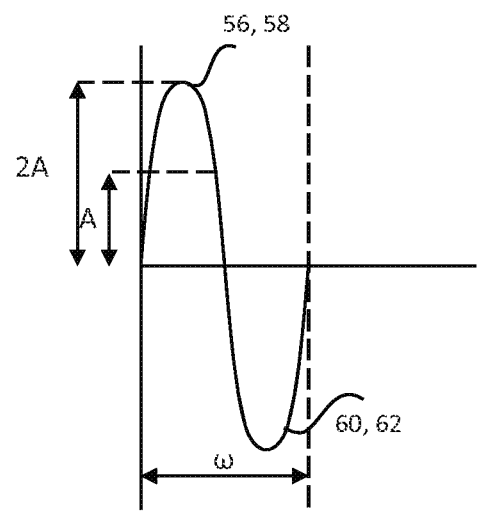
Figure 4C:
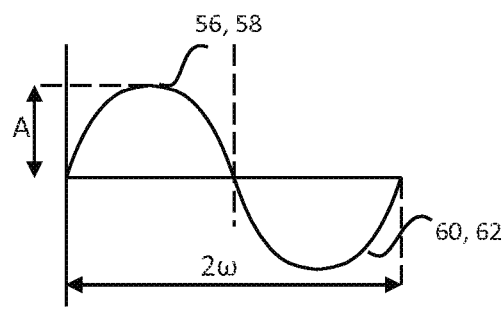

FIGS. 4A-4C illustrate various exemplary embodiments where the oscillations in lumens 52 and 54 may extend as sinusoidal oscillations having a plurality of crests and troughs with defined amplitudes (A) and angular frequencies ($\omega$). As shown, each of the amplitude and frequency (or both) may be adjusted to vary the path of the lumens 52, 54, which in turn varies the amount of slack in the cables extending through the lumens. As shown for example in FIG. 4A, the lumens of the implantable lead 14 extend as sinusoidal oscillations having crests 56, 58 and troughs 60, 62 defining an amplitude of A and a frequency of $\omega$. As shown for example in FIG. 4B, the lumens of the implantable lead 14 extend as sinusoidal oscillations having crests 56, 58 and troughs 60, 62 defining an amplitude of 2 A and a frequency of $\omega$. As shown for example in FIG. 4C, the lumens of the implantable lead 14 extend as sinusoidal oscillations having crests 56, 58 and troughs 60, 62 defining an amplitude of A and a frequency of $2\omega$.

The amplitudes and frequencies may be selected and optimized to configure the desired sinusoidal oscillations in the lumens 52 and 54 such that the oscillations provide a desired about of slack in the conductor cables to minimize or prevent strain in the conductor cables during bending motion. In exemplary embodiments of the present disclosure, the amplitudes (A) and frequencies ($\omega$) of the lumens 52 and 54 may be optimized throughout the length of the lead 14. In other embodiments of the present disclosure, the amplitudes and frequencies of the lumens 52 and 54 may be optimized in desired portions of the lead 14. In some embodiments of the present disclosure, for example, in portions of the lead 14 that are prone to substantial bending, the lumens 52 and 54 are configured to have an increased amplitude or frequency (or both) to allow for further slack in the conductor cable. Further, various parameters of the lead 14 may be taken into consideration in selecting the optimized amplitude and frequency including, for example, materials of the lead 14, materials of the conductor cables, length of the lead 14, diameter of the lead 14, diameter of the conductor cables, bending angles of the conductor cables, and axial tension in the conductor cables. According to exemplary embodiments, a portion of the lead near the terminal connector includes oscillating lumens.

According to some embodiments, a portion of the lead body extending from about 10 mm to about 50 mm from the terminal connector includes oscillating lumens. According to other embodiments, a portion of the lead body extending from about 10 mm to about 25 mm from the terminal connector includes oscillating lumens. According to other embodiments, a portion of the lead body extending about 20.32 mm from the terminal connector includes oscillating lumens. In the various disclosed embodiments, the lumens may have a variety of amplitudes and angular frequencies. According to various exemplary embodiments, the oscillating lumens have amplitudes of about 1 mm and an angular frequency of about 0.309 mm, which results in a lumen length of about 20.8 mm. In these embodiments, the lumen thus allow for an excess length of about 0.48 mm (i.e., 20.8 mm minus 20.32 mm), which allows for strain relief for a conductor placed within the lumen. It will be apparent to a person of ordinary skill in the art that various other parameters may be taken into consideration without deviating from the scope of the invention. According to various embodiments, the oscillating lumens have amplitudes of between about 0.1 and about 2.0 mm. According to various embodiments the oscillating lumens have an angular frequency of between about 0.1 and about 0.7 mm.

Figure 5A:
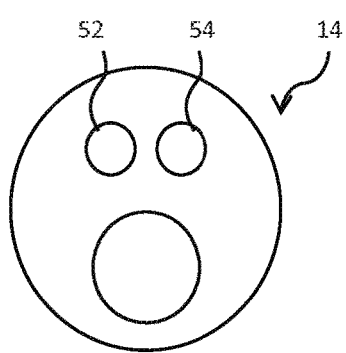
FIGS. 5A-5D illustrate cross-sectional views of the electrical implantable lead that includes plurality of oscillating lumens according to various embodiments.
Figure 5B:
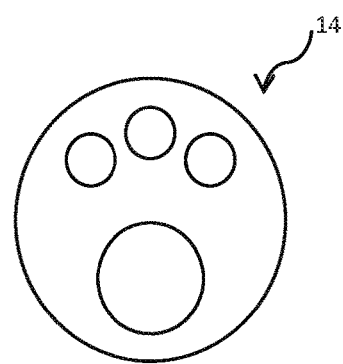
Figure 5C:
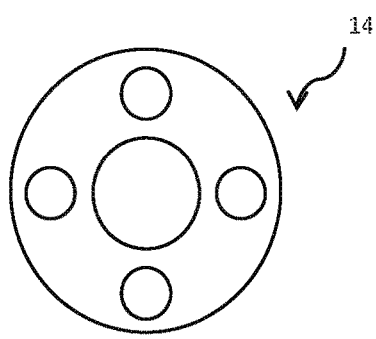
Figure 5D:
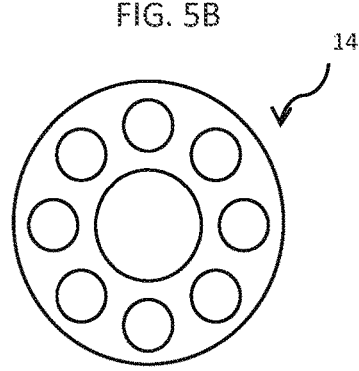

FIGS. 5A-5D illustrate cross-sectional views of an electrical implantable lead 14 including a plurality of oscillating lumens 52, 54 according to various embodiments. As shown in FIG. 5A, the lead 14 includes two oscillating lumens 52, 54 that are radially offset from center axis of the lead 14. FIG. 5B shows a lead 14 having three oscillating lumens radially offset from the center axis of the lead 14. FIG. 5C shows the lead body 14 with four oscillating lumens that radially offset from the central axis of the lead 14 and generally equally spaced about a circumference of the lead body. FIG. 5D shows the lead body 14 with plurality of oscillating lumens that are radially offset from the central axis of the lead 14 and generally equally spaced about a circumference of the lead body.

FIGS. 6A-6E illustrate exemplary methods 210 and 220 for manufacturing the electrical implantable lead 14 using injection molding techniques. In these embodiments, lumens may or may not be formed within the lead 14. In other words, the conductors may be molded directly into the lead 14 or a temporary structure (e.g., a Nitinol wire) may be used during the molding process and then removed to expose a lumen which may then be later loaded with a conductor. Thus, while the following description refers to directly forming the conductor within the lead 14, the disclosed methods may also be used to form lumens into which a conductor may be later inserted.

Figures 6A, 6B:
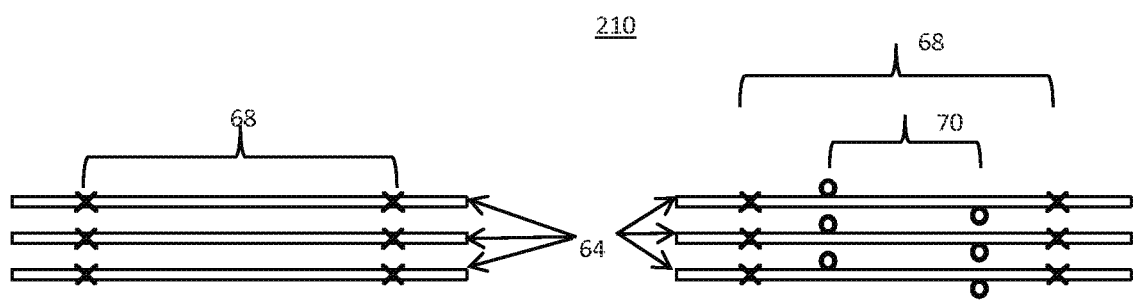
FIGS. 6A-6E illustrate a system for manufacturing the electrical implantable lead according to a disclosed embodiment.
Figure 6C:
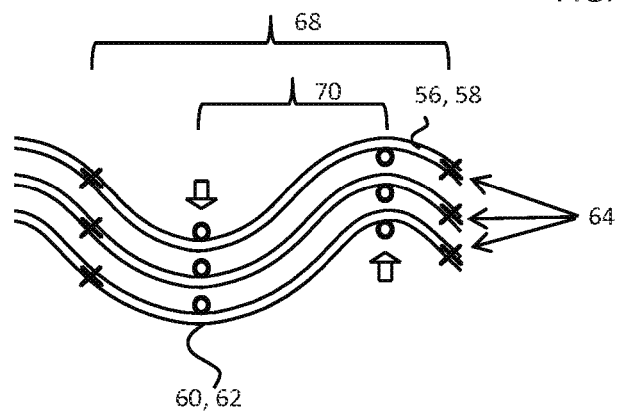

FIGS. 6A-6C illustrate a method 210 for manufacturing the implantable lead 14. As shown in FIG. 6A, a plurality of holding pins 68 hold or support a plurality of conductor cables 64 in tension in a mold. FIG. 6B shows a plurality of guiding pins 70 disposed between the plurality of the conductor cables 64. FIG. 6C shows translation of the guiding pins 70 to impart a non-linear (e.g., W-shaped, undulating, or oscillating) configuration to the conductor cables 64. This non-linear configuration may include a series of crests 56, 58 and troughs 60, 62 of desired amplitude and frequency. In some embodiments, the desired amplitude and frequency may be achieved by increasing or decreasing the number of guiding pins or changing the lateral offset (e.g., spacing from a longitudinal centerline of the lead) between successive guiding pins 70. Once the conductor cables 64 are held in the desired configuration by the holding pins 68 and the guiding pins 70, the lead body is formed by standard injection molding techniques as are known in the art. After the lead body is formed by injection molding, the holding pins 68 and guiding pins 70 may be removed. The resulting spaces or lumens may be filled with a suitable material (e.g., silicone rubber or medical adhesive), to complete the formation of the lead body. The method shown with reference to FIGS. 6A-6C will create a lead 14 having a configuration as shown in FIG. 8.

Figure 6D:
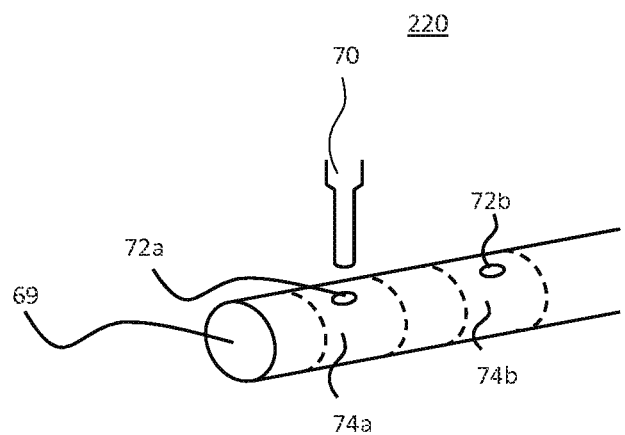
Figure 6E:
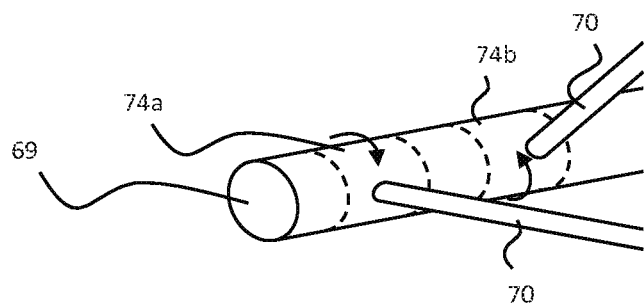

FIGS. 6D-6E illustrate a method 220 for manufacturing an implantable lead 14. As shown in FIG. 6D, a major lumen core pin 69 includes holes 72*a*, 72*b* to support the guiding pins 70 located in dynamic sections 74*a*, 74*b*. As shown in FIG. 6E, the guiding pins 70 are inserted into the holes 72*a*, 72*b* and are then used to rotate the dynamic sections 74 in opposite directions. The dynamic sections 74 may be rotated with the guiding pins 70 about a longitudinal axis of the core pin 69 a sufficient amount to achieve the desired amplitude and frequency. This technique may be used to impart a non-linear configuration, which may be either planar or three dimensional.

Figure 7:
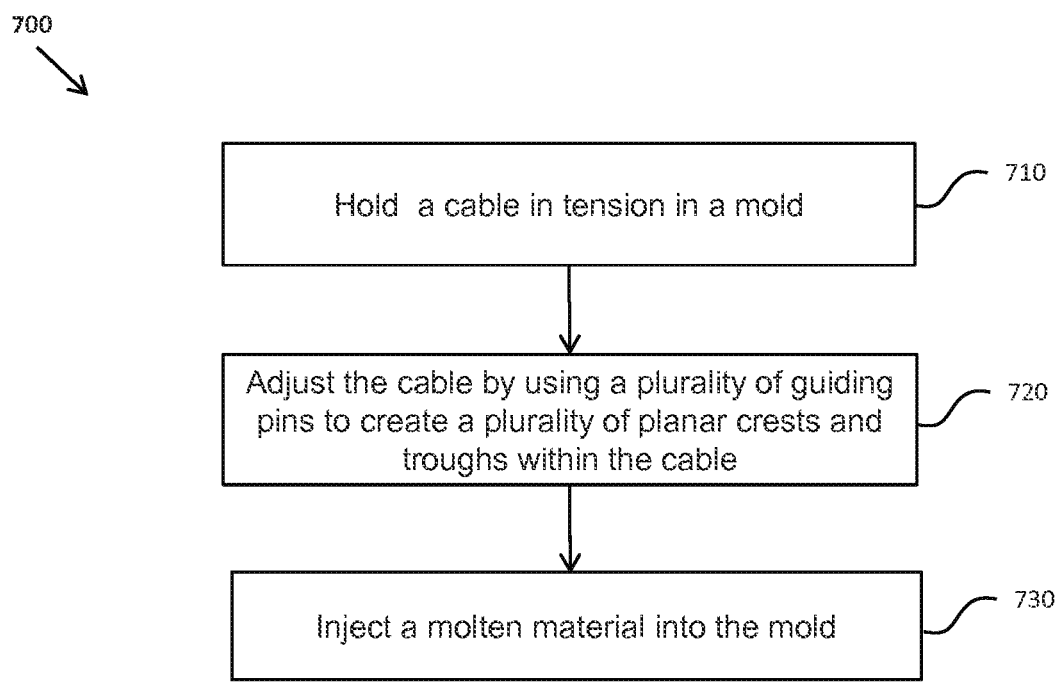
FIG. 7 is a flowchart depicting an exemplary method for manufacturing an electrical implantable lead or a portion of the lead.

FIG. 7 is a flowchart showing an exemplary method 700 for manufacturing an electrical implantable lead 14 (or a segment of the lead 14). The method 700 begins with holding a cable (or conductor such as, for example Nitinol) in tension in a mold (step 710). According to various embodiments, the cable may be made from nickel-cobalt-chromium-molybdenum alloys (e.g., MP35N), silver alloys, tantalum alloys, or any other material commonly used in conductors for an implantable medical lead. In various embodiments, the cable includes an insulating coating, which may include a lubricious coating. Next, the cable is adjusted using a plurality of guiding pins to create a plurality of planar crests and troughs within the cable (step 720). After creating the crests and troughs within the cable, a molten material may be injected into the mold (step 730). In various embodiments, the molten material may be Liquid Silicone Rubber (LSR). The molten material is cured to set the series of crests and troughs within the cable. The method 700 may further include removing the cable from the mold such that a lumen with the series of crests and troughs is created. The method 700 may further include filling holes created by the plurality of guiding pins with LSR or a medical adhesive.

Figure 8A:
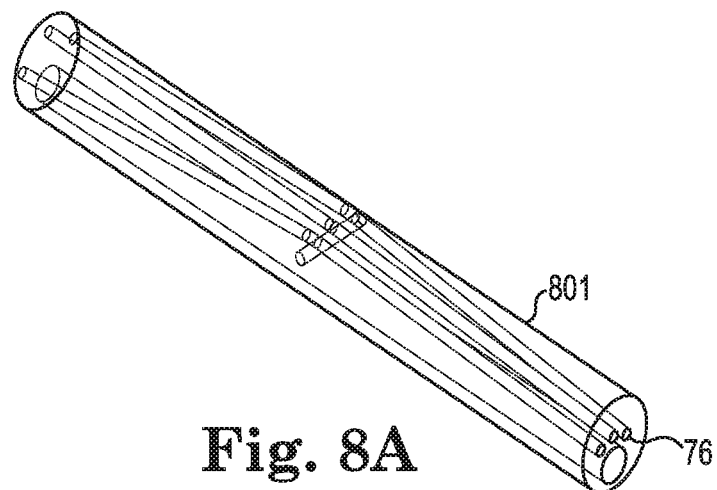
FIGS. 8A-8B illustrate implantable electrical lead segments having different oscillating lumen orientations according to various embodiments.
Figure 8B:
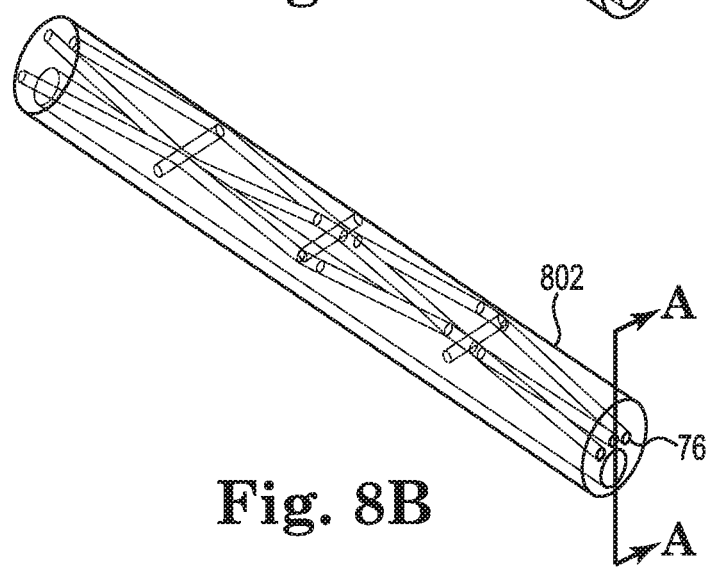
Figure 8C:
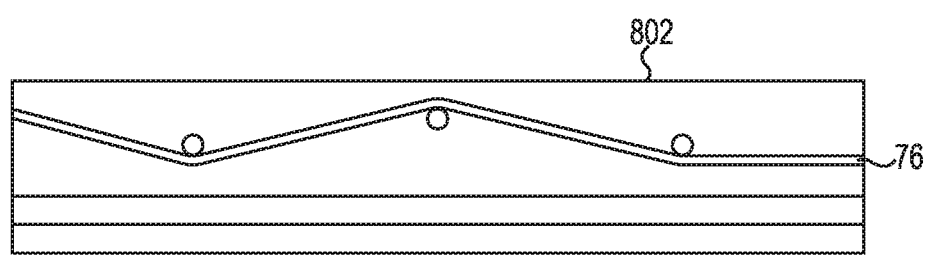
FIG. 8C illustrates a cross-sectional side view of FIG. 8B along line A-A.

Exemplary lead segments resulting from the process of method 700 are shown in FIGS. 8A-8C. As shown in FIG. 8A, the lead segment 801 includes three conductor lumens 76 having the same (or substantially the same) angular frequency ($\omega$), with one conductor lumen 76 having a first amplitude and two conductor lumens having a second, greater amplitude. According to various embodiments, the configuration of the lead segment 801 includes one lumen 76 having an amplitude of A and two lumens 76 having and amplitude of 2 A, such as shown for example in FIGS. 4A and 4B. As shown in FIG. 8B, the lead segment 802 includes three conductor lumens 76 having the same (or substantially the same) angular frequency ($\omega$), with two of the conductor lumens 76 having a first amplitude and a third conductor lumen 76 having a generally opposite amplitude. FIG. 8C shows a cross-sectional side view along line A-A of FIG. 8B showing the lead segment 802 and the path of conductor lumen 76 in a plane.

Figure 9:
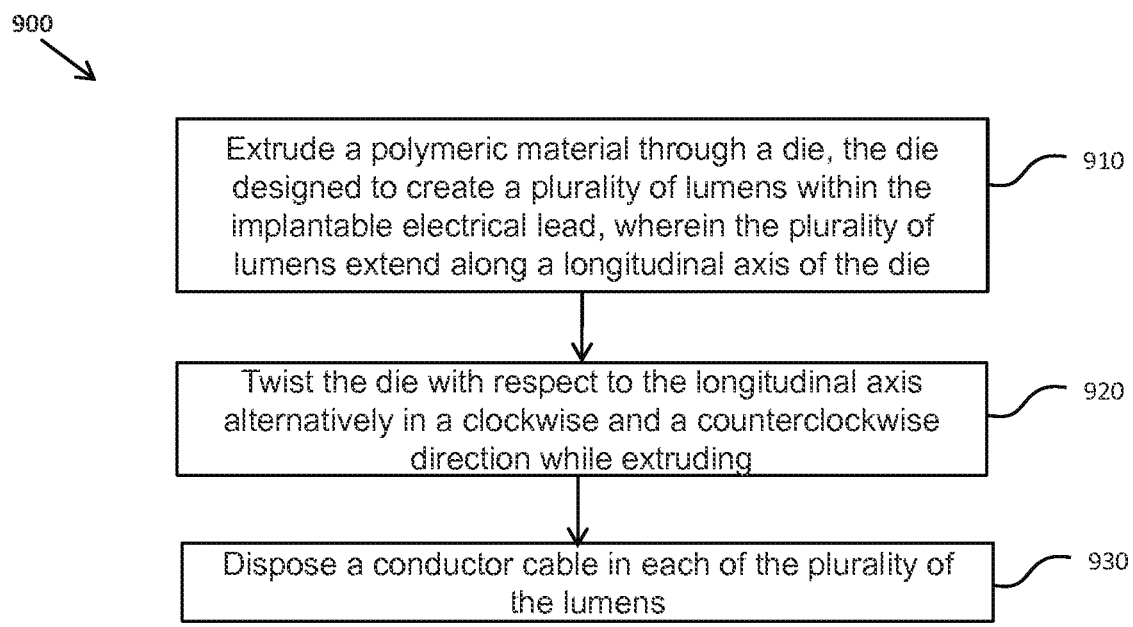
FIG. 9 is a flowchart illustrating an exemplary method for manufacturing an electrical implantable lead or a portion of the lead.
Figure 10:
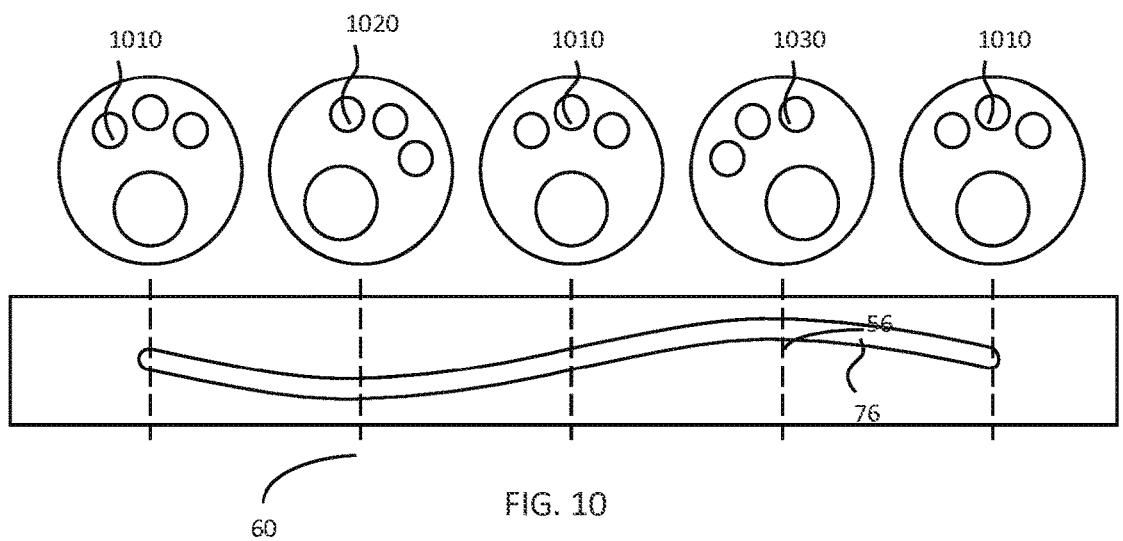
FIG. 10 is a schematic view showing various cross-sections of an electrical implantable lead having an oscillating lumen.

FIG. 9 is a flowchart showing an exemplary method 900 for manufacturing an electrical implantable lead 14 according to another embodiment of the present disclosure. The method begins with extruding a polymeric material through a die including pins (further described with respect to FIG. 10) to form lumens (step 910). In various embodiments, the die and pins are designed to create a plurality of lumens within the implantable electrical lead. These lumens extend along a longitudinal axis of the die. Next, the die and pins are twisted (i.e., rotated) with respect to the longitudinal axis alternatively in a clockwise and a counterclockwise direction while extruding (step 920), such that twisting in the clockwise direction creates a trough and twisting in the counterclockwise direction creates a crest in the plurality of the lumens. Then, a conductor cable may be inserted into each of the plurality of the lumens (step 930). FIG. 10 is a schematic view further illustrating the method 900. As shown in FIG. 10, the method 900 results in a lead (or lead segment) having an oscillating lumen 76 formed along a longitudinal axis of the lead. As shown at 1010, extrusion of the lead begins with the die and pins in a first position. Then, as extrusion of the lead body continues, the die and pins are rotated in a clockwise direction to clockwise position 1020, a trough 60 is formed in the lumen 76. Next, as extrusion continues, the die and pins are rotated counterclockwise through the original position 1010 and further to counterclockwise position 1030, which forms a crest 56 in the lumen 76. Finally, the dies and pins are rotated clockwise back to the original position 1010. This process may then be repeated as desired to create further oscillations in the lumen 76. The relative speed of extrusion (i.e., longitudinal extension of the lead body) and rotation of the die and pins determine the angular frequency of the lumen 76, and the degree of rotation of the die and pins determine the amplitude of the lumen 76.

Figure 11:
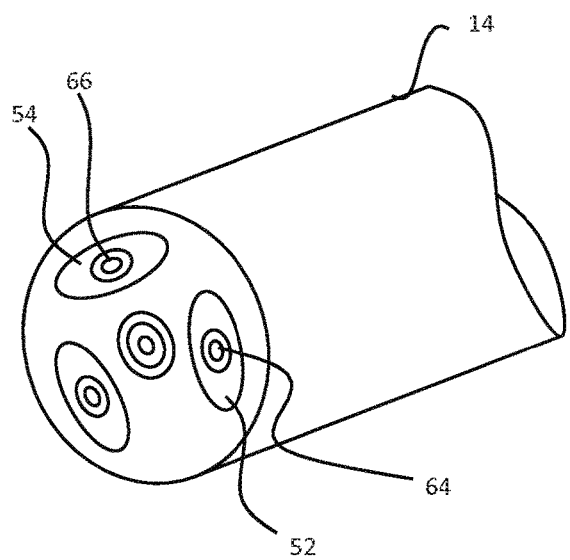
FIG. 11 illustrates a perspective view of a portion of the electrical implantable lead with lumens according to various embodiments.

FIG. 11 is a perspective view of a lead 14 according to other disclosed embodiments. As shown in FIG. 11, the lead 14 (or lead segment) includes a plurality of lumens 52, 54 having an oval- or elliptical-shaped cross-section. According to various embodiments, this structure is formed by extruding a lead body segment having lumens with oval- or elliptical-shaped cross-sections. As shown, this oval- or elliptical-shaped cross-section allows the conductors (e.g., cables) 64, 66 located within the lumens 52, 54 to have a non-linear (e.g., oscillating or sinusoidal) configuration.

Figure 12:
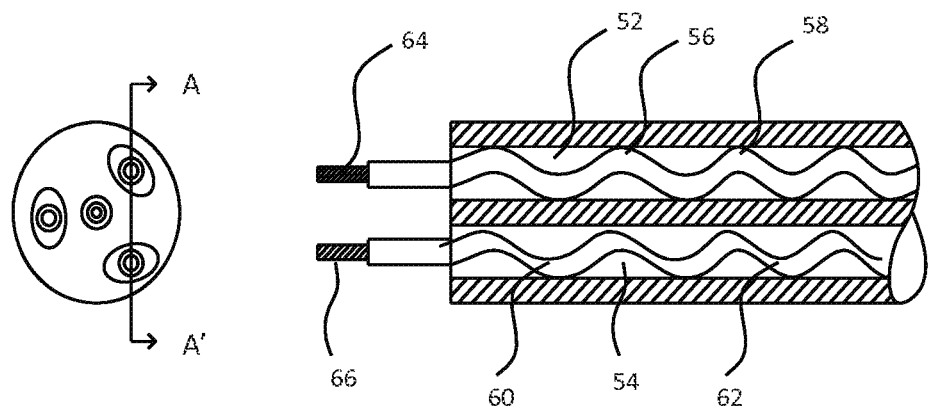
FIG. 12 illustrates a perspective view of a portion of the electrical implantable lead that includes a linear lumen and oscillating conductor cables.

As shown in FIG. 12, in these embodiments, the lumens 52, 54 follow a generally straight or linear path along the longitudinal axis of the lead 14. As shown in FIG. 12, the conductor cables 64, 66, disposed within the plurality of lumens 52, 54, having an inherent undulating or non-linear shape. In various embodiments, the non-linear shape of the conductors or cables 64, 66 includes a plurality of crests 56, 58 and troughs 60, 62. These crests and troughs in the cables may be similar to the sinusoidal oscillations illustrated and explained in conjunction with previous embodiments related to the crests and the troughs of the non-linear lumens of FIGS. 2-10. In accordance with the embodiments shown in FIGS. 11 and 12, the undulating or non-linear pattern of the conductor cables provides a slack to the conductor cables, which provides relief during bending of the lead. In accordance with these embodiments, and as illustrated in FIGS. 11 and 12, the diameter of the lumens 52, 54 are equal to or greater than the amplitude of the conductors or cables 64, 66.

The undulating or non-linear conductors 64, 66 described in conjunction with FIGS. 11 and 12 may be formed according to any of a variety of methods. According to exemplary embodiments, the method includes coating a cable with a thermoplastic such as for example ethylene tetrafluoroethylene (ETFE) or polytetrafluoroethylene (PTFE). The coated cables are then inserted into a die having a defined shape (e.g., oscillating or sinusoidal). The method further includes heating the coated cables to set the shape of the thermoplastic material. In some embodiments, the die can have a sinusoidal shape. The amplitude and frequency of the sinusoidal shape may be selected to optimize flex performance and stringability of the cables in the lead body lumens. In other embodiments, the cables coated with a thermoplastic are forced into a helix, spiral, or coil shape by wrapping the coated cables around a mandrel. The mandrel is then heated sufficiently to heat-set the thermoplastic coating such that cables retain the spiral shape after the mandrel is removed. In other embodiments, the undulations in the cable are formed by placing the cable into a die defining the desired shape, then overmolding the cables with a polymer (e.g., silicone rubber) to maintain the desired shape. According to other embodiments, the undulating or non-linear shape is imparted to the conductors by bending the conductors past their yield point such that the conductors retain the desired shape. This bending may be accomplished, for example by bending the cable around a small diameter pin. In other embodiments, the method of manufacturing may involve stringing a straight cable into a larger diameter lumen and then pushing a part of the cable extending outside the lead body into the lumen, which will cause the cable to buckle and undulate inside the lumen.

Figure 13:
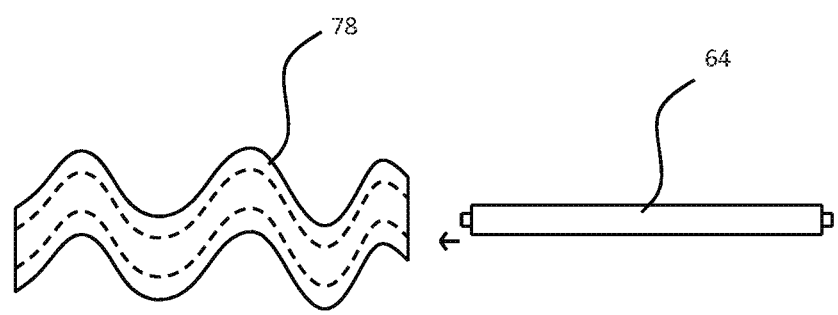
FIG. 13 illustrates an exemplary method for manufacturing an electrical implantable lead or a portion of the lead.

FIG. 13 shows another embodiment for forming undulations in a cable. As shown, a cable 64 is inserted into a polymer tube 78 having a preformed oscillating or undulating shape. According to some embodiments, the polymer tube 78 is formed by molding a polymer (e.g., silicone rubber or polyurethane) over an undulating mandrel or core. As the cable 64 is inserted into the undulating polymer tube 78, it takes on the undulating shape of the polymer tube 78. In another exemplary embodiment, a molded lead or terminal boot with undulating cables can be manufactured by injecting silicone rubber (or polyurethane or similar elastomeric polymer with low durometer between Shore 60D and 40A) over core pins that have a sinusoidal shape. The core pins are then removed to create lumens. When silicone rubber is used for molding, the molded part can be swelled in heptane or hexane. For other polymers that are not easily swelled, if the core pins are easily malleable, they may be put in tension until they are approximately straight and capable of being pulled out. In some embodiments, the core pins are provided with a low friction coating (e.g., PTFE) to facilitate removal. In other embodiments, the core pins are made out of a shape memory alloy having an undulating austentitic shape and a straight martensitic shape. In these embodiments, the core pin can be used in an overmolding process, then placed in a cold temperature environment (e.g., dipped in cold water) to straighten the core pin to facilitate removal.

After the conductors or cable are formed into a non-linear (e.g., oscillating, undulating, etc.) shape using a technique described herein, the conductors are inserted into the oval or elliptical lumens. According to embodiments where the cable or conductor is formed as a spiral or helix, the corresponding lumen in the lead body may also have a circular shape having a sufficiently large diameter to accept the cable or conductor in its spiral or helical shape. The resulting structure provides for a cable or conductor having an overall length greater than a length of the lumen, which helps minimize stress (and thus fatigue) during bending of the lead.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

We claim:

1. A method of manufacturing an implantable medical lead, the method comprising:
    extruding a polymeric material through a die configured to create a plurality of lumens within the implantable medical lead, wherein the plurality of lumens extend along a longitudinal axis of the die;
    twisting the die with respect to the longitudinal axis alternatively in a clockwise direction and a counterclockwise direction while extruding such that twisting in the clockwise direction creates a trough and in the counterclockwise direction creates a crest in the plurality of lumens; and
    inserting a conductor cable in each of the plurality of lumens.

2. The method of claim 1, wherein some portions of the plurality of lumens extend longitudinally clockwise and other portions of the plurality of lumens extend longitudinally counterclockwise.

3. The method of claim 1, wherein at least some of the plurality of lumens have a circular cross-section.

4. The method of claim 1, wherein the crest and the trough define a sinusoidal pattern with a defined amplitude and a defined angular frequency.

5. The method of claim 1, wherein the crest and the trough are formed in a rotational plane in a three-dimensional manner.

6. The method of claim 1, wherein the plurality of lumens extend longitudinally in a rotational plane, the rotational plane being defined about the longitudinal axis of the die.

7. A method of manufacturing an implantable medical lead, the method comprising:
    holding a cable in tension in a mold while supporting the cable using a plurality of guiding pins such that the cable forms a plurality of planar crests and troughs within the mold; and
    injecting a molten material into the mold to form a lead body around the cable, wherein the cable extends longitudinally along a portion of the lead body.

8. The method of claim 7, further comprising removing the cable from the mold leaving a lumen with the plurality of planar crests and troughs in the lead body.

9. The method of claim 8, further comprising inserting a conductor into the lumen.

10. The method of claim 8, wherein the lumen extends longitudinally in a linear, two-dimensional plane.

11. The method of claim 8, wherein the lumen has a circular cross-section.

12. The method of claim 7, wherein the cable includes at least one of:
    a conductor cable;
    a Nitinol wire;
    a cable with a lubricious coating.

13. The method of claim 7, wherein the molten material is a first molten material, the method further comprising filling holes created by the plurality of guiding pins with either the first molten material or a second molten material.

14. The method of claim 7, wherein the molten material is a first molten material, the method further comprising filling holes created by the plurality of guiding pins with a second molten material, wherein the second molten material is one of a group consisting of:
    a medical adhesive; and
    a liquid silicone rubber.

15. The method of claim 7, wherein the molten material is a liquid silicone rubber.

16. A method of manufacturing an implantable medical lead, the method comprising:
    overmolding silicone rubber having a durometer of between about Shore 60D and about Shore 40A over a core pin to form a lead body,
    wherein the core pin is made of a shape memory metal, the core pin having a first generally sinusoidal configuration and a second generally linear configuration, and
    wherein the overmolding silicone rubber over the core pin to form the lead body comprises injecting silicone rubber over the core pin while the core pin is in the first generally sinusoidal configuration within a mold;
    cooling the core pin such that the core pin is in the second generally linear configuration;
    removing the core pin from the lead body so that the lead body defines a lumen having a generally sinusoidal configuration; and
    inserting a conductor into the lumen.

17. The method of claim 16,
    wherein the core pin is made out of a shape memory alloy, and
    wherein the shape memory alloy provides an undulating austenitic shape corresponding to the first generally sinusoidal configuration.

18. The method of claim 17, wherein the shape memory alloy provides straight martensitic shape corresponding to the second generally linear configuration.

19. The method of claim 16, wherein the lumen extends longitudinally in a linear, two-dimensional plane.

20. The method of claim 16, wherein the lumen has a circular cross-section.

* * * * *